United States Patent [19]

Teranishi et al.

[11] Patent Number: 5,116,739
[45] Date of Patent: May 26, 1992

[54] PROCESS FOR THE PRODUCTION OF HUMAN APOLIPOPROTEIN E, AND TRANSFORMED HOSTS AND PRODUCTS THEREOF

[75] Inventors: Yutaka Teranishi, Sagamihara; Nobuhiko Takamatsu; Yasushi Matsui, both of Yokohama; Masako Kimura, Nakano; Yasuko Ikeda, Sagamihara; Yuuki Morimoto, Machida, all of Japan

[73] Assignee: Mitsubishi Chemical Industries Limited, Tokyo, Japan

[21] Appl. No.: 288,470

[22] Filed: Dec. 22, 1988

Related U.S. Application Data

[63] Continuation of Ser. No. 754,050, Jul. 11, 1985, abandoned.

[30] Foreign Application Priority Data

Oct. 16, 1984 [JP] Japan ............................. 59-216987
Jun. 11, 1985 [JP] Japan ............................. 60-126989

[51] Int. Cl.$^5$ .................. C12P 21/02; C12N 5/06; C12N 15/12
[52] U.S. Cl. .................. 435/69.6; 435/320.1; 435/240.2; 435/172.3; 935/34; 935/70
[58] Field of Search ........... 435/320, 69.6, 320.1, 435/240.2, 172.3; 536/27; 935/11, 28, 29, 32; 530/350

[56] References Cited

U.S. PATENT DOCUMENTS

| | | | |
|---|---|---|---|
| 4,332,892 | 6/1982 | Ptashine et al. | 435/68 |
| 4,446,235 | 5/1984 | Seeburg | 435/91 |
| 4,578,355 | 3/1986 | Rosenberg | 435/317 |
| 4,613,572 | 9/1986 | MacKay et al. | 435/253 |
| 5,059,528 | 10/1991 | Bollen et al. | 435/69.4 |

FOREIGN PATENT DOCUMENTS

WO87/02062 4/1987 PCT Int'l Appl.

OTHER PUBLICATIONS

Scahill et al. (1983), Proc. Natl. Acad. Sci., vol. 83, pp. 4654-4658.
Pavlakis et al. (1983), Proc. Natl. Acad. Sci., vol. 80, pp. 397-401.
Crowley et al. (1983), Mol. Cell. Biol., vol. 3, pp. 44-55.
Gorman et al. (1984), Phil. Trans. R. Soc. Lond. B, vol. 307, pp. 343-346.
Breslow et al. *J. Biol. Chem.* 257(24):14639-14641, 1982 (Dec.).
McLean et al. *J. Biol. Chem.* 257(10):6498-6504, 1984 (May).
Zannis et al. *J. Biol. Chem.* 259(8):5495-5499, 1984 (Apr.).
Paik et al. *Proc. Natl. Acad. Sci. USA* 82:3445-3449, 1985 (May).

Primary Examiner—Richard A. Schwartz
Assistant Examiner—Richard M. Lebovitz
Attorney, Agent, or Firm—Foley & Lardner

[57] ABSTRACT

The invention provides DNA fragments coding for human apolipoprotein E or human apolipoprotein E-like substances having physiological activities equivalent to those of said human apolipoprotein E, expression vectors suitable for production of such proteins, hosts for use in the production, and process for the production, as well as such proteins thereby produced.

4 Claims, 14 Drawing Sheets

FIG. 2a

| FIG.2a |
|---|
| FIG.2b |
| FIG.2c |

```
                                                      -18
                                                      Met Lys Val Leu Trp Ala Ala Leu Leu Val Thr Phe Leu Ala Gly Cys Gln Ala
TCACAGGCAGGAAG                                        ATG AAG GTT CTG TGG GCT GCA CTG CTG GTC ACA TTC CTG GCA GGA TGC CAG GCA

-1   1
                                                                                Lys Val
                                                                                AAG GTG 10                                              20
Glu Gln Ala Val Glu Thr Glu Pro Glu Pro Glu Leu Arg Gln Gln Thr Glu Trp Gln Ser Gly Gln Arg Trp
GAG CAA GCG GTG GAG ACA GAG CCG GAG CCC GAG CTG CGC CAG CAG ACC GAG TGG CAG AGC GGC CAG CGC TGG 30                                                  40                                              50
Glu Leu Ala Leu Gly Arg Phe Trp Asp Tyr Leu Arg Trp Val Gln Thr Leu Ser Glu Gln Val Gln Glu Glu
GAA CTG GCA CTG GGT CGC TTT TGG GAT TAC CTG CGC TGG GTG CAG ACA CTG TCT GAG CAG GTG CAG GAG GAG 60                                              70
Leu Leu Ser Ser Gln Val Thr Gln Glu Leu Arg Ala Leu Met Asp Glu Thr Met Lys Glu Leu Lys Ala Tyr
CTG CTC AGC TCC CAG GTC ACC CAG GAA CTG AGG GCG CTG ATG GAC GAG ACC ATG AAG GAG TTG AAG GCC TAC 80                                              90
Lys Ser Glu Leu Glu Glu Gln Leu Thr Pro Val Ala Glu Glu Thr Arg Ala Arg Leu Ser Lys Glu Leu Gln
AAA TCG GAA CTG GAG GAG CAA CTG ACC CCG GTG GCG GAG GAG ACG CGG GCA CGG CTG TCC AAG GAG CTG CAG 100                                             110                                             120
Ala Ala Gln Ala Arg Leu Gly Ala Asp Met Glu Asp Val Cys Gly Arg Leu Val Gln Tyr Arg Gly Glu Val
GCG GCG CAG GCC CGG CTG GGC GCG GAC ATG GAG GAC GTG TGC GGC CGC CTG GTG CAG TAC CGC GGC GAG GTG
```

FIG. 2b

|   |   |   |   |   |   | 130 |   |   |   |   |   |   |   |   | 140 |   |   |   |   |
|---|---|---|---|---|---|---|---|---|---|---|---|---|---|---|---|---|---|---|---|

```
    Gln Ala Met Leu Gly Gln Ser Thr Glu Glu Leu Arg Val Arg Leu Ala Ser His Leu Arg Lys Leu Arg Lys
    CAG GCC ATG CTC GGC CAG AGC ACC GAG GAG CTG CGG GTG CGC CTC GCC TCC CAC CTG CGC AAG CTG CGT AAG 150                                         160                         170
    Arg Leu Arg Asp Ala Asp Leu Gln Lys Arg Leu Ala Val Tyr Gln Ala Gly Arg Glu Gly Ala
    CGG CTC CGC GAT GCC GAT CTG CAG AAG CGC CTG GCA GTG TAC CAG GCC GGG CGC GAG GGC GCC

Glu Arg Gly Leu Ser Ala Ile Arg Glu Leu Gly Pro Leu Val Glu Gln Gly Arg Val Arg Ala Ala Thr
    GAG CGC GGC CTC AGC GCC ATC CGC GAG CTG GGG CCC CTG GTG GAA CAG GGC CGC GTG CGG GCC GCC ACT 200                                     210
    Val Gly Ser Leu Ala Gly Gln Pro Leu Gln Ala Arg Ala Gln Ala Trp Gly Glu Arg Leu Arg Ala Arg Met
    GTG GGC TCC CTG GCC GGG CAG CCG CTA CAG GCC CGG GCC CAG GCC TGG GGC GAG CGG CTG CGC GCG CGG ATG 230                                 240
    Glu Glu Met Gly Ser Arg Thr Arg Asp Arg Leu Asp Glu Val Lys Glu Val Ala Glu Val Arg Ala Lys
    GAG GAG ATG GGC AGC CGG ACC CGC GAC CGC CTG GAC GAG GTG AAG GAG GTG GCG GAG GTG CGC GCC AAG 250                                         260
    Leu Glu Glu Gln Ala Gln Gln Ile Arg Leu Arg Leu Gln Ala Phe Gln Ala Glu Ala Arg Leu Lys Ser Trp Phe Glu
    CTG GAG GAG CAG GCC CAG CAG ATA CGC CTG CGC CTG CAG GCC TTC CAG GCC GAG GCC CGC CTC AAG AGC TGG TTC GAG
```

FIG.2c

```
                    270                         280                              290
Pro Leu Val Glu Asp Met Gln Arg Gln Trp Ala Gly Leu Val Glu Lys Val Gln Ala Ala Val Gly Thr Ser
CCC CTG GTG GAA GAC ATG CAG CGC CAG TGG GCC GGG CTG GTG GAG AAG GTG CAG GCT GCC GTG GGC ACC AGC

300
Ala Ala Pro Val Pro Ser Asp Asn His term
GCC GCC CCT GTG CCC AGC GAC AAT CAC TGA    ACGCCGAAGCCTGCAGCCATGCGACCCCACGCCACCCCGTGCCTCCTGCCTCCG CGCAGCCTGCAGCGGGGAGACCCTGTCCCCGCCCCAGCCGTCCTCCTGGGGTGACCCTAGTTTAATAAAGATTCACCAAGTTTCACGC
```

H : Hind III
E : EcoR I
P : Pst I
X : Xba I
B : BamH I

PROCESS FOR THE PRODUCTION OF HUMAN APOLIPOPROTEIN E, AND TRANSFORMED HOSTS AND PRODUCTS THEREOF

This is a continuation of application Ser. No. 06/754,050, filed Jul. 11, 1985, now abandoned.

FIELD OF THE INVENTION

This invention relates to DNA fragments coding for human apolipoprotein E or human apolipoprotein E-like substances having physiological activities equivalent to those of said human apolipoprotein E (hereinafter referred to as human apolipoprotein E-like proteins), expression vectors suitable for production of such proteins, hosts for use in the production and process for the production, as well as such proteins thereby produced.

DESCRIPTION OF PRIOR ART

Lipids in plasma consist essentially of cholesterol, phospholipids, triglycerides and free fatty acids. These lipids except the last one are conjugated with proteins, so that water-insoluble lipids are solubilized in plasma. Such lipid-protein complexes, which are called lipoproteins, have various molecular weights depending on the proportion of the lipid to the protein. Lipoproteins have globular structures which may be considered to be composed of nonpolar triglycerides or cholesterol esters as a core and polar phospholipids or free cholesterol forming a superficial layer in association with proteins.

Proteins contained in lipoproteins are called apolipoproteins and ten or more apolipoproteins are known at present. Apolipoproteins are essential constituents of lipoproteins and play an important role in the metabolism of lipoproteins as well.

Apolipoprotein E is one of the known apolipoproteins. It is also known that apolipoprotein E acts as a recognition marker when the lipoproteins are incorporated through a receptor into cells in a living body.

In addition, three main subclasses E2, E3 and E4 have been found in the apolipoprotein E. Apolipoprotein E3 may be derived from normal human beings, while the subclasses E2 and E4 were found in patients with hyperlipidemia type III and are considered to be of non-normal type: The Journal of Biological Chemistry, Vol. 255, No. 5, 1759-1762 (1980).

Either those who are deficient in apolipoprotein E3 or those who have apolipoprotein E2 or E4 often suffer from hyperlipidemia resulting in arteriosclerosis. The normal functions of the apolipoprotein E in such patients can be recovered by administration of normal apolipoprotein E3.

In order to obtain apolipoprotein E through recombinant DNA technique, it is necessary to isolate DNA coding for apolipoprotein E. However, a full length cDNA fragment required for obtaining entire apolipoprotein E have not been got yet.

We have now obtained the full length cDNA fragment necessary for the production of apolipoprotein E and succeeded in expression of the fragment by inserting it into an expression vector suitable for the production of the desired protein.

SUMMARY OF THE INVENTION

This invention provides a DNA fragment containing a base sequence which codes for human apolipoprotein E and represented by the following formula (I):

```
AAG GTG GAG CAA GCG GTG GAG ACA GAG CCG GAG CCC GAG CTG CGC      (I)
CAG CAG ACC GAG TGG CAG AGC GGC CAG CGC TGG GAA CTG GCA CTG
GGT CGC TTT TGG GAT TAC CTG CGC TGG GTG CAG ACA CTG TCT GAG
CAG GTG CAG GAG GAG CTG CTC AGC TCC CAG GTC ACC CAG GAA CTG
AGG GCG CTG ATG GAC GAG ACC ATG AAG GAG TTG AAG GCC TAC AAA
TCG GAA CTG GAG GAA CAA CTG ACC CCG GTG GCG GAG GAG ACG CGG
GCA CGG CTG TCC AAG GAG CTG CAG GCG GCG CAG GCC CGG CTG GGC
GCG GAC ATG GAG GAC GTG TGC GGC CGC CTG GTG CAG TAC CGC GGC
GAG GTG CAG GCC ATG CTC GGC CAG AGC ACC GAG GAG CTG CGG GTG
CGC CTC GCC TCC CAC CTG CGC AAG CTG CGT AAG CGG CTC CTC CGC
GAT GCC GAT GAC CTG CAG AAG CGC CTG GCA GTG TAC CAG GCC GGG
GCC CGC GAG GGC GCC GAG CGC GGC CTC AGC GCC ATC CGC GAG CGC
CTG GGG CCC CTG GTG GAA CAG GGC CGC GTG CGG GCC GCC ACT GTG
GGC TCC CTG GCC GGC CAG CCG CTA CAG GAG CGG GCC CAG GCC TGG
GGC GAG CGG CTG CGC GCG CGG ATG GAG GAG ATG GGC AGC CGG ACC
CGC GAC CGC CTG GAC GAG GTG AAG GAG CAG GTG GCG GAG GTG CGC
GCC AAG CTG GAG GAG CAG GCC CAG CAG ATA CGC CTG CAG GCC GAG
GCC TTC CAG GCC CGC CTC AAG AGC TGG TTC GAG CCC CTG GTG GAA
GAC ATG CAG CGC CAG TGG GCC GGG CTG GTG GAG AAG GTG CAG GCT
GCC GTG GGC ACC AGC GCC GCC CCT GTG CCC AGC GAC AAT CAC
``` or a base sequence which codes for a human apolipoprotein E-like protein.

Also provided is an expression vector containing, downstream of a promoter, a structural gene which codes for at least a portion of the human apolipoprotein E or human apolipoprotein E-like protein.

The present invention further provides human apolipoprotein E having the amino acid sequence represented by the following formula (II):

| Lys | Val | Glu | Gln | Ala | Val | Glu | Thr | Glu | Pro | Glu | Pro | Glu | Leu | Arg | (II) |
|-----|-----|-----|-----|-----|-----|-----|-----|-----|-----|-----|-----|-----|-----|-----|------|
| Gln | Gln | Thr | Glu | Trp | Gln | Ser | Gly | Gln | Arg | Trp | Glu | Leu | Ala | Leu | |
| Gly | Arg | Phe | Trp | Asp | Tyr | Leu | Arg | Trp | Val | Gln | Thr | Leu | Ser | Glu | |
| Gln | Val | Gln | Glu | Glu | Leu | Leu | Ser | Ser | Gln | Val | Thr | Gln | Glu | Leu | |
| Arg | Ala | Leu | Met | Asp | Glu | Thr | Met | Lys | Glu | Leu | Lys | Ala | Tyr | Lys | |
| Ser | Glu | Leu | Glu | Glu | Gln | Leu | Thr | Pro | Val | Ala | Glu | Glu | Thr | Arg | |
| Ala | Arg | Leu | Ser | Lys | Glu | Leu | Gln | Ala | Ala | Gln | Ala | Arg | Leu | Gly | |
| Ala | Asp | Met | Glu | Asp | Val | Cys | Gly | Arg | Leu | Val | Gln | Tyr | Arg | Gly | |
| Glu | Val | Gln | Ala | Met | Leu | Gly | Gln | Ser | Thr | Glu | Glu | Leu | Arg | Val | |
| Arg | Leu | Ala | Ser | His | Leu | Arg | Lys | Leu | Arg | Lys | Arg | Leu | Leu | Arg | |
| Asp | Ala | Asp | Asp | Leu | Gln | Lys | Arg | Leu | Ala | Val | Tyr | Gln | Ala | Gly | |

-continued

| Ala | Arg | Glu | Gly | Ala | Glu | Arg | Gly | Leu | Ser | Ala | Ile | Arg | Glu | Arg |
|-----|-----|-----|-----|-----|-----|-----|-----|-----|-----|-----|-----|-----|-----|-----|
| Leu | Gly | Pro | Leu | Val | Glu | Gln | Gly | Arg | Val | Arg | Ala | Ala | Thr | Val |
| Gly | Ser | Leu | Ala | Gly | Gln | Pro | Leu | Gln | Glu | Arg | Ala | Gln | Ala | Trp |
| Gly | Glu | Arg | Leu | Arg | Ala | Arg | Met | Glu | Glu | Met | Gly | Ser | Arg | Thr |
| Arg | Asp | Arg | Leu | Asp | Glu | Val | Lys | Glu | Gln | Val | Ala | Glu | Val | Arg |
| Ala | Lys | Leu | Glu | Glu | Gln | Ala | Gln | Gln | Ile | Arg | Leu | Gln | Ala | Glu |
| Ala | Phe | Gln | Ala | Arg | Leu | Lys | Ser | Trp | Phe | Glu | Pro | Leu | Val | Glu |
| Asp | Met | Gln | Arg | Gln | Trp | Ala | Gly | Leu | Val | Glu | Lys | Val | Gln | Ala |
| Ala | Val | Gly | Thr | Ser | Ala | Ala | Pro | Val | Pro | Ser | Asp | Asn | His |     | or a human apolipoprotein E-like protein, which is produced by recombinant DNA technique.

The invention also provides a host transformed with an expression vector containing a structural gene which codes for at least a portion of human apolipoprotein E or human apolipoprotein E-like protein.

The invention still further provides a process for preparing human apolipoprotein E or a human apolipoprotein E-like protein, which comprises introducing, into a host, an expression vector containing a structural gene that codes for at least a portion of the human apolipoprotein E or human apolipoprotein E-like protein, culturing the transformed host, and collecting the protein produced.

BRIEF DESCRIPTION OF THE DRAWINGS

The invention will be fully described with reference to the attached drawings in which:

FIG. 2a-c shows the base sequence of the DNA fragment of the invention and the amino acid sequence deduced therefrom;

DETAILED DESCRIPTION OF THE INVENTION

Figure 1:
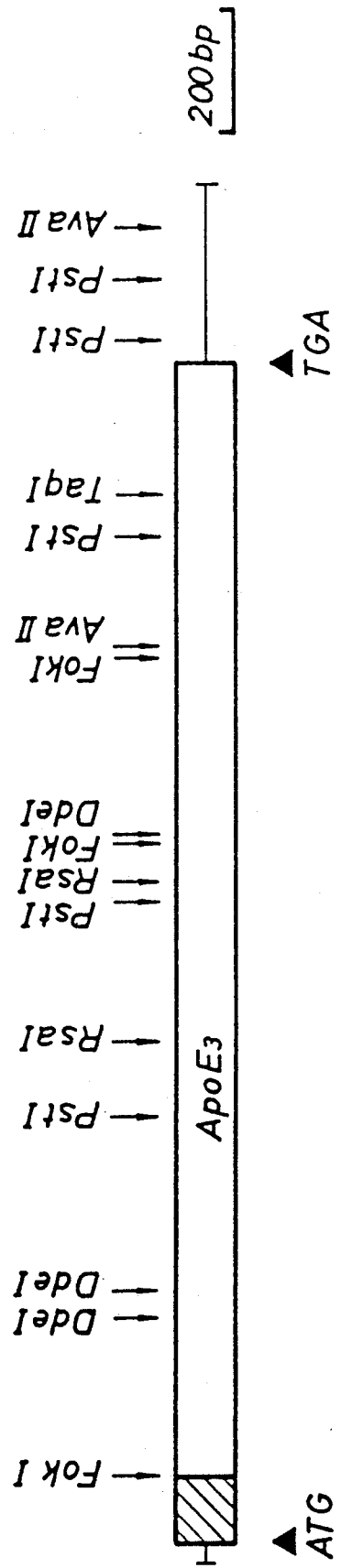
FIG. 1 shows the restriction enzyme cleavage map of plasmid pYAE10 into which a DNA fragment of the invention has been inserted.

A DNA fragment containing DNA sequence which codes for human apolipoprotein E3 may be prepared in the following manner.

Human-derived specimens of liver sections, small intestine epidermal cells, blood macrophages or kidney sections are homogenized in the presence of guanidinyl thiocyanate and total RNA is separated by CsCl. equilibrium density gradient ultracentrifugation: Chirgwin et al., Biochemistry, 18, 5294–5299 (1979). The total RNA is purified by conventional oligo(dT) cellulose column chromatography to isolate poly(A)-containing RNAs which are used as mRNA materials.

The mRNA materials are treated by the method described by Okayama and Berg in Molecular and Cellular Biology, 2, 161–170 (1982) to prepare cDNA library. A vector primer and an oligo(dG)-tailed linker are obtained from a hybrid plasmid of pBR322 and SV40. The vector primer and the mRNA materials are used to synthesize cDNAs in the presence of reverse transcriptase. The cDNAs are digested with HindIII and then cyclized together with the linker. Subsequently, the mRNA portions are substituted by DNAs to obtain cDNA fragment-containing plasmids.

The plasmids are used to transform *Escherichia coli* or other microorganism in a conventional manner. The resulting ampicillin resistant transformants are screened using as a probe a synthetic oligonucleotide containing a portion or whole portion of the base sequence which corresponds to the amino acid sequence at the positions 218–222 of apolipoprotein E (Met-Glu-Glu-Met-Gly) or a synthetic oligonucleotide containing at least said base sequence. Thus, clones containing a base sequence complementary to said base sequence are selected. Plasmids from the clones are treated with appropriate restriction enzymes to select clones containing a plasmid into which the longest cDNA has been inserted.

The base sequence of cDNA fragment from the clones is determined by the method of Maxam and Gilbert: Methods in Enzymology, 65, 499–560 (1980).

The base sequence which codes for human apolipoprotein E is represented by the following formula (I):

```
AAG GTG GAG CAA GCG GTG GAG ACA GAG CCG GAG CCC GAG CTG CGC    (I)
CAG CAG ACC GAG TGG CAG AGC GGC CAG CGC TGG GAA CTG GCA CTG
GGT CGC TTT TGG GAT TAC CTG CGC TGG GTG CAG ACA CTG TCT GAG
CAG GTG CAG GAG GAG CTG CTC AGC TCC CAG GTC ACC CAG GAA CTG
AGG GCG CTG ATG GAC GAG ACC ATG AAG GAG TTG AAG GCC TAC AAA
TCG GAA CTG GAG GAA CAA CTG ACC CCG GTG GCG GAG GAG ACG CGG
GCA CGG CTG TCC AAG GAG CTG CAG GCG GCG CAG GCC CGG CTG GGC
GCG GAC ATG GAG GAC GTG TGC GGC CGC CTG GTG CAG TAC CGC GGC
GAG GTG CAG GCC ATG CTC GGC CAG AGC ACC GAG GAG CTG CGG GTG
CGC CTC GCC TCC CAC CTG CGC AAG CTG CGT AAG CGG CTC CTC CGC
GAT GCC GAT GAC CTG CAG AAG CGC CTG GCA GTG TAC CAG GCC GGG
GCC CGC GAG GGC GCC GAG CGC GGC CTC AGC GCC ATC CGC GAG CGC
CTG GGG CCC CTG GTG GAA CAG GGC CGC GTG CGG GCC GCC ACT GTG
GGC TCC CTG GCC GGC CAG CCG CTA CAG GAG CGG GCC CAG GCC TGG
GGC GAG CGG CTG CGC GCG CGG ATG GAG GAG ATG GGC AGC CGG ACC
CGC GAC CGC CTG GAC GAG GTG AAG GAG CAG GTG GCG GAG GTG CGC
GCC AAG CTG GAG GAG CAG GCC CAG CAG ATA CGC CTG CAG GCC GAG
GCC TTC CAG GCC CGC CTC AAG AGC TGG TTC GAG CCC CTG GTG GAA
GAC ATG CAG CGC CAG TGG GCC GGG CTG GTG GAG AAG GTG CAG GCT
GCC GTG GGC ACC AGC GCC GCC CCT GTG CCC AGC GAC AAT CAC
```

The DNA fragments according to the invention contain DNA coding for apolipoprotein E or an apolipoprotein E-like protein. One example of such fragments is shown in FIG. 2. However, the present invention is not limited to those having the same sequences as shown in FIG. 2. Any DNA fragment in which a portion of the base sequence (I) is substituted by other base(s) or deleted or one or more bases are added to the base sequence (I) may be encompassed in the invention as long as DNA contained in such a fragment codes for an apolipoprotein E-like protein which has physiological activities equivalent to those of said apolipoprotein E. For example, protein-synthesis initiation codon, ATG, can be chemically added to 5' end of the base sequence (I).

Any DNA fragment corresponding to a non-normal subclass E2 or E4 may be prepared in a similar manner from liver sections or others of patients with E2 or E4.

The expression vectors of the invention may be prepared by inserting the DNA fragment, which contains a base sequence coding for at least a portion of said apolipoprotein E or apolipoprotein E-like protein, into a cloning site of an expression vector which has a promoter (expression regulatory region) upstream of the cloning site.

The cloning site is preferably a restriction enzyme recognition site which enables direct expression of a desired foreign gene. Preferably, BamHI site immediately before translational initiation codon is utilized. BamHI site can be formed using a synthetic linker when no BamHI site exists downstream of the promoter.

Preferred promoters include those which can be regulated by lacI: for example, the promoter of lpp gene coding for one of *E. coli* outer membrane proteins (lipoprotein); tac promoter which is a fused promoter of trp promoter with lac promoter [Proceeding of National Academy Science, 80, 21 (1983)]; or the promoter of ompF gene. In addition, $P_R$ and $P_L$ promoters of $\lambda$ phage may preferably be utilized as well.

Also, promoters derived from yeast may preferably be utilized; for example, the promoters of GAL1, GAL10, HIS4, CYC, ADR2, PYK and PGK genes. Further, SV40 early or late promoter, the promoter of human metallothionein gene or heat shock protein gene, or the like may also be preferred in the invention. In particular, when an expression vector contains both the origin of replication (ORI) of SV40 virus and SV40 early or late promoter, animal cells such as COS, CHO and others can be utilized as a host.

Illustrative examples of the cloning site in expression vectors containing such a promoter as described above are: PvuII site of plasmid pGL101 containing lac promoter [Proc. Natl. Acad. Sci., 77, 5230 (1980)]; BamHI site of plasmid pDR720 containing trp promoter (P. L., Biochemicals); and BglII site of plasmid pMA91 containing the promoter of PGK (phosphoglycerokinase) gene [Gene, 24, 1 (1983)].

The expression vectors of the invention should contain an origin of replication (ORI) which enables their replication in a host. The ORI which may be employed includes those of *E. coli* plasmid pBR322, yeast 2 μm DNA, SV40 virus, papilloma virus and the like, as well as ars (autonomously replicating sequence) containing the origin of replication of yeast chromosome.

The expression vectors of the invention should also contain a selective marker so that hosts transformed therewith can be selected. The selective markers include resistance gene to antibiotics, such as ampicillin, tetracycline, chloramphenicol, kanamycin and the like; genes capable of complementing mutations of *E. coli*, such as HIS3, TRP1, LEU2, URA3 and the like; HSV tk, aprt, DHFR and other genes which are utilized for eukaryotic cells.

For the expression of a gene coding for at least a portion of human apolipoprotein E or apolipoprotein E-like protein which is inserted into a cloning site of the vector of the invention, both the transcriptional direction and the translational frame of the promoter and gene should coincide in direction and phase, respectively. The coincidence of the transcriptional direction may preferably be attained using two different restriction enzyme recognition sites present in the vector. In order to obtain the coincidence of the translational frame of the promoter and gene in phase, the homopolymer tailing method, the addition method of 1, 2 or 4 bases to 5' end of the gene in a conventional manner, or the like can be utilized.

The expression level can be enhanced by modifying the distance between Shine-Dalgarno sequence in the transcription control region of a prokaryotic vector and the translational initiation codon. The use of an expression vector into which a gene coding for a signal peptide of ompF, β-lactamase, alkaline phosphatase or other gene is inserted upstream of the structural gene enables secretion of apolipoprotein E into either culture medium (through the bacterial cell membrane) or the periplasma.

When an eukaryotic expression vector is employed, insertion of an exon-intron junction region of β-globin or other gene into the vector can enhance the expression level of apolipoprotein E gene. One example of such expression vectors is a plasmid pKCRH2 [Nature, 307, 604 (1984)], into which a junction region consisting of 5' splice junction donor site containing 5' terminal region of β-globin gene, intron, and 3' splice junction donor site containing 3' terminal region of the gene has been inserted downstream of SV40 promoter. Apolipoprotein E gene can be cloned into HindIII site at 3' end of the junction region. The junction region is not necessarily adjacent to the promoter; it may be inserted downstream of a structural gene.

The expression vectors of the invention are introduced into hosts. The transformed hosts may then be cultured in a conventional manner to produce desired proteins. The desired human apolipoprotein E is represented by the following formula (II):

| | | | | | | | | | | | | | | |
|---|---|---|---|---|---|---|---|---|---|---|---|---|---|---|
| Lys | Val | Glu | Gln | Ala | Val | Glu | Thr | Glu | Pro | Glu | Pro | Glu | Leu | Arg | (II)
| Gln | Gln | Thr | Glu | Trp | Gln | Ser | Gly | Gln | Arg | Trp | Glu | Leu | Ala | Leu |
| Gly | Arg | Phe | Trp | Asp | Tyr | Leu | Arg | Trp | Val | Gln | Thr | Leu | Ser | Glu |
| Gln | Val | Gln | Glu | Glu | Leu | Leu | Ser | Ser | Gln | Val | Thr | Gln | Glu | Leu |
| Arg | Ala | Leu | Met | Asp | Glu | Thr | Met | Lys | Glu | Leu | Lys | Ala | Tyr | Lys |
| Ser | Glu | Leu | Glu | Glu | Gln | Leu | Thr | Pro | Val | Ala | Glu | Glu | Thr | Arg |
| Ala | Arg | Leu | Ser | Lys | Glu | Leu | Gln | Ala | Ala | Gln | Ala | Arg | Leu | Gly |
| Ala | Asp | Met | Glu | Asp | Val | Cys | Gly | Arg | Leu | Val | Gln | Tyr | Arg | Gly |
| Glu | Val | Gln | Ala | Met | Leu | Gly | Gln | Ser | Thr | Glu | Glu | Leu | Arg | Val |
| Arg | Leu | Ala | Ser | His | Leu | Arg | Lys | Leu | Arg | Lys | Arg | Leu | Leu | Arg |
| Asp | Ala | Asp | Asp | Leu | Gln | Lys | Arg | Leu | Ala | Val | Tyr | Gln | Ala | Gly |
| Ala | Arg | Glu | Gly | Ala | Glu | Arg | Gly | Leu | Ser | Ala | Ile | Arg | Glu | Arg |
| Leu | Gly | Pro | Leu | Val | Glu | Gln | Gly | Arg | Val | Arg | Ala | Ala | Thr | Val |

-continued

| Gly | Ser | Leu | Ala | Gly | Gln | Pro | Leu | Gln | Glu | Arg | Ala | Gln | Ala | Trp |
|-----|-----|-----|-----|-----|-----|-----|-----|-----|-----|-----|-----|-----|-----|-----|
| Gly | Glu | Arg | Leu | Arg | Ala | Arg | Met | Glu | Glu | Met | Gly | Ser | Arg | Thr |
| Arg | Asp | Arg | Leu | Asp | Glu | Val | Lys | Glu | Gln | Val | Ala | Glu | Val | Arg |
| Ala | Lys | Leu | Glu | Glu | Gln | Ala | Gln | Gln | Ile | Arg | Leu | Gln | Ala | Glu |
| Ala | Phe | Gln | Ala | Arg | Leu | Lys | Ser | Trp | Phe | Glu | Pro | Leu | Val | Glu |
| Asp | Met | Gln | Arg | Gln | Trp | Ala | Gly | Leu | Val | Glu | Lys | Val | Gln | Ala |
| Ala | Val | Gly | Thr | Ser | Ala | Ala | Pro | Val | Pro | Ser | Asp | Asn | His |     |

In addition, the proteins produced according to the invention may include human apolipoprotein E-like proteins, that is, those substances having physiological activities equivalent to those of said human apolipoprotein E (II). The proteins may be produced in the form of either fused proteins or mature proteins, for example, human apolipoprotein having Met at N-terminal thereof.

The hosts which may be employed in the invention include *E. coli* HB101, JM106, etc.; yeast DBY746, AH22, 20B12, etc. (East Genetic Stock Center, U.S.A.); *Bacillus subtilis* and the like. In addition to such microorganisms, animal cells such as COS, CHO, etc. can also be employed in the invention.

The proteins thus produced may be collected and purified in any conventional manner.

ADVANTAGES OF THE INVENTION

According to the invention, human apolipoprotein E or human apolipoprotein E-like proteins can be efficiently produced. The obtained proteins, apolipoprotein E2, E3 or E4, may be used as antigens to prepare antisera by a usual method. The antisera can be employed to detect the deficiency of normal apolipoprotein E3 or the presence of non-normal type E2 or E4.

The apolipoprotein E3 obtained may be used as an anti-hyperlipidemia or anti-arteriosclerosis agent.

DESCRIPTION OF THE PREFERRED EMBODIMENTS

The invention will be more fully illustrated with reference to the following examples. However, many modifications and variations will be apparent to those skilled in the art and it should be understood that such modifications and variations are included within the scope of the present invention.

In the examples, treatments with restriction enzymes or modification enzymes were carried out according to specifications by the manufacturers and distributors (TAKARA SHUZO Co. Ltd., New England Biolabs). Transformations of *E. coli* were preformed in accordance with the method described in "Molecular Cloning", p. 250, Cold Spring Harbor Laboratories (1982).

EXAMPLE 1

Preparation of DNA Fragment (1) Preparation of mRNA

After crushing human liver sections in liquid nitrogen, an aqueous solution of guanidinium thiocyanate was added and homogenized. The homogenate was applied to cesium chloride equilibrium density gradient ultracentrifugation according to Chirgwin et al. method described in Biochemistry, 18, 5294-5299 (1979) to separate total RNA. This was purified by oligo(dT) cellulose column chromatography in a conventional method to isolate poly(A)-containing RNA which was used as mRNA material.

(2) Preparation of Vector Primer and Oligo(dG)-tailed Linker

Vector primer and oligo(dG)-tailed linker were prepared from hybrid plasmid of pBR322 and SV40 by Okayama and Berg method described in Molecular and Cellular Biology, 2, 161-170 (1982).

Hybrid plasmid (400 μg) of pBR322 and SV40 (map units 0.71-0.86) was digested with KpnI at 37° C. for 4 hours in a buffer containing bovine serum albumin. DNA was collected by conventional ethanol precipitation. The DNA was then dissolved in a buffer containing dTTP and terminal deoxynucleotidyl transferase was added. After the reaction was carried out at 37° C. for 30 minutes, about 60 dT tail was added to the KpnI-digested end. DNA was then collected by ethanol precipitation.

The DNA was digested with HpaI at 37° C. for 5 hours in a buffer containing bovine serum albumin. Larger DNA fragment was purified by agarose gel electrophoresis and collected by the glass powder method described by Vogelstein et al. in Proc. Natl. Acad. Sci. U.S.A., 76, 615-619 (1979). The DNA fragment was applied to oligo(dA) cellulose column at 0° C., eluted with water, and collected with ethanol. Thus, vector primer having an oligo(dT) tail was obtained.

On the other hand, hybrid plasmid (100 μg) of pBR322 and SV40 (map units 0.19-0.32) was digested with PstI at 37° C. for one hour and a half in a buffer containing bovine serum albumin. DNA was collected and dissolved again in a buffer containing dGTP. Terminal deoxynucleotidyl transferase was added to the solution and reacted at 37° C. for 20 minutes so that about 10-15 dG tail was added to the DNA. The DNA was then collected and digested with HindIII at 37° C. for one hour in a buffer containing bovine serum albumin. Small oligo(dG)-tailed linker DNA was extracted and collected by 1.8% agarose gel electrophoresis.

(3) Preparation of cDNA Library

According to Okayama and Berg method described in Molecular and Cellular Biology, 2, 161-170 (1982), cDNA library was obtained.

To an aqueous solution containing Tris-HCl, pH 8.3, MgCl$_2$, KCl, dithiothreitol, dATP, dTTP, dGTP and [$^{32}$P]dCTP, 30 μg the mRNA material obtained in (1) above and 10 μg of the vector primer obtained in (2) above were added and reacted at 37° C. for 20 minutes in the presence of reverse transcriptase. The thus synthesized plasmid cDNA:mRNA was precipitated with ethanol and collected in the form of pellets.

The pellets were dissolved in a buffer containing CoCl$_2$, dithiothreitol, poly(A), [$^{32}$P]dCTP and terminal deoxynucleotidyl transferase, and reacted at 37° C. for 10 minutes so that 10-15 dCMP residues were added to each end. The collected pellets containing oligo(dC)-tailed plasmid cDNA:mRNA were dissolved again in a buffer containing bovine serum albumin, digested with HindIII at 37° C. for one hour and precipitated with ethanol.

The HindIII-digested oligo(dC)-tailed cDNA:mRNA plasmid thus collected was re-dissolved in a buffer containing the oligo(dG)-tailed linker DNA obtained in (2) above, incubated at 65° C. for 2 minutes and then at 42° C. for 30 minutes, and thereafter cooled to 0° C. E. coli DNA ligase was added and incubated overnight in the presence of β-NAD (nicotin adenine dinucleotide). After adding dATP, dTTP, dGTP, dCTP, β-NAD, E. coli DNA polymerase and E. coli DNA polymerase and E. coli RNase H, the mixture was incubated at 12° C. for one hour and then at room temperature for one hour. After cooling the reaction was terminated. Thus, the desired cDNA fragment-containing plasmid was obtained.

(4) Cloning and Sequencing

The plasmid was used to transform E. coli HB101 in a conventional method.

Screening was performed according to Hanahan et al. method described in Gene, 10, 63-67 (1980) using four snythetic oligonucleotides:

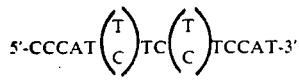

as a probe. These oligonucleotides correspond to the amino acid sequence at the positions 218-222 of apolipoprotein E: Met-Glu-Glu-Met-Gly. About 50 clones containing sequences complementary to the synthetic oligonucleotides were selected from about 100,000 transformants.

Fourteen of the selected clones were treated with several restriction enzymes and 3 clones were found to have common recognition sites by the restriction enzymes. The largest clone pYAE10 was chosen for determination of the base sequence by Maxam and Gilbert method.

The restriction enzyme cleavage map made in order to determine the base sequence of the clone pYAE10 is shown in FIG. 1 wherein ATG is translational initiation codon and TGA is translational termination codon. FIG. 2 shows the determined base sequence of the DNA fragment and the amino acid sequence deduced therefrom (the number of amino acid residues: 317 residues). The DNA fragment corresponds to apolipoprotein E3 (ApoE3) from a normal human being.

EXAMPLE 2

Production of Human Apolipoprotein E-like Proteins

Figure 3:
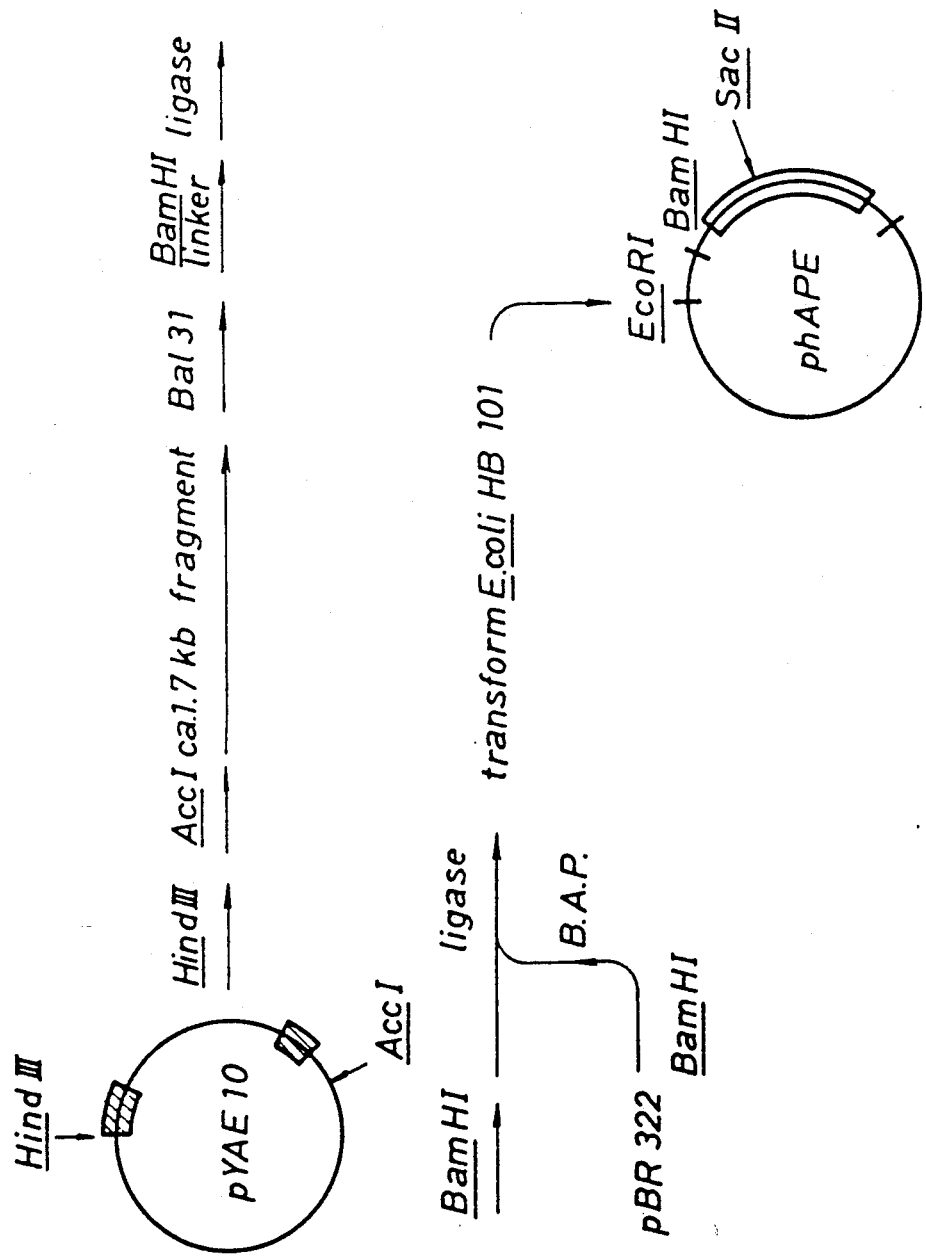
FIGS. 3 to 8a-b show the construction of plasmids phAPE, phAPE-1, pIN-tac, phAPE-2, phAPE-3 and phAPE-4, respectively.

A. Construction of Expression Plasmids (1) Construction of Plasmid phAPE (FIG. 3)

The plasmid pYAE10 obtained in Example 1 was digested with HindIII and AccI at 37° C. for 2 hours. The resulting 1.7 kb fragment was treated with Ba131 at 37° C. for 15 minutes, ligated to BamHI linker in the presence of T4 DNA polymerase at 15° C. for 14 hours, and digested with BamHI at 37° C. for 2 hours.

On the other hand, pBR322 was digested with BamHI at 37° C. for 2 hours and treated with B.A.P. at 37° C. for one hour.

Two fragments thus obtained were ligated using T4 DNA ligase at 14° C. for 16 hours. E. coli HB101 was transformed and plasmid phAPE was obtained from the transformant.

Figure 4:
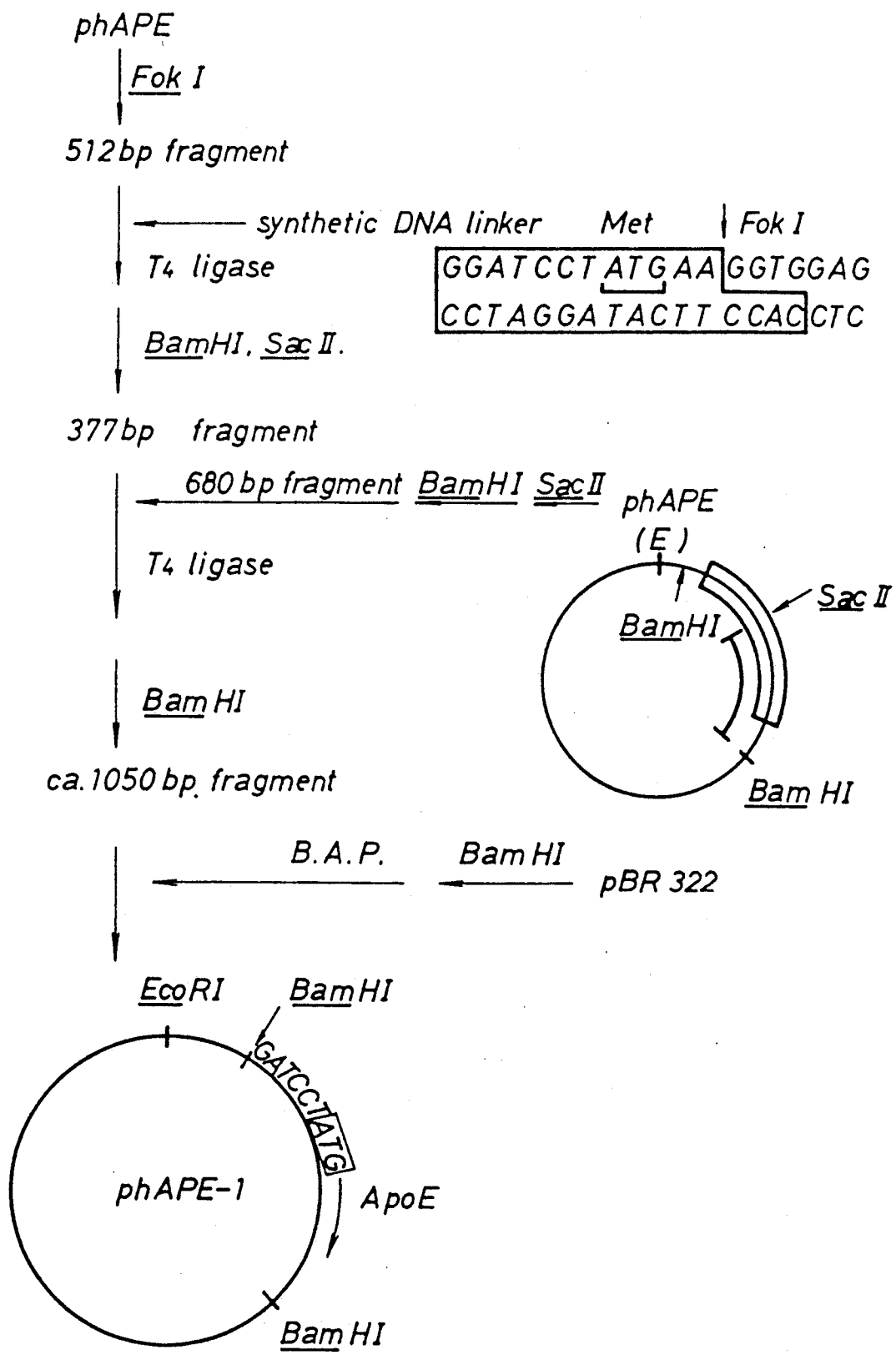

(2) Construction of Plasmid phAPE-1 (FIG. 4)

The plasmid phAPE was digested with FokI at 37° C. for 2 hours. The resulting 512 bp fragment was ligated to a synthetic DNA linker:

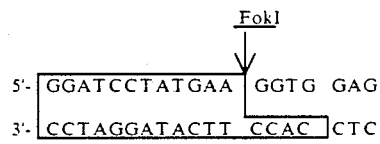

in the presence of T4 DNA ligase at 8° C. for 16 hours. The resulting fragment was digested with BamHI and SacII at 37° C. for 2 hours to obtain 377 bp fragment.

On the other hand, the plasmid phPPE was digested with SacII and BamHI at 37° C. for 2 hours. The resulting 680 bp fragment was ligated to the 377 bp fragment at 14° C. for 8 hours in the presence of T4 DNA ligase and digested with BamHI to obtain about 1050 bp fragment.

Plasmid pBR322 was digested with BamHI at 37° C. for 2 hours and treated with B.A.P. Into the resulting fragment the about 1050 bp fragment was introduced to obtain plasmid phAPE-1.

Figure 5:
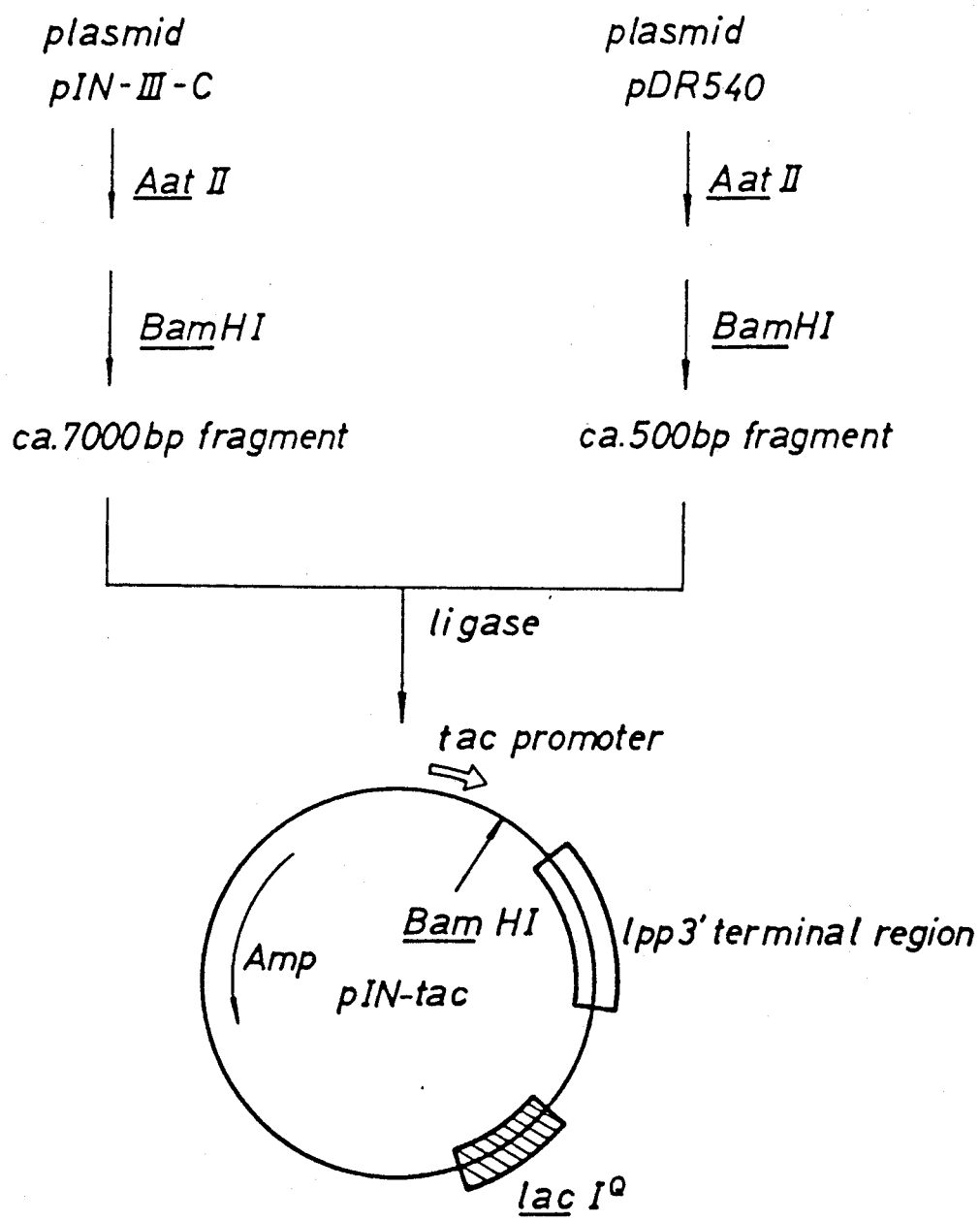

(3) Construction of Plasmid pIN-tac (FIG. 5)

Plasmid pIN-III-C (Experimental Manipulation of Gene Expression, Edited by M. Inouye, 1983, Academic Press, p. 15) was digested with AatII and BamHI at 37° C. for 2 hours to obtain about 7000 bp fragment. On the other hand, plasmid pDR540 (purchasable from P. L. Biochemicals) was digested with AatII and BamHI at 37° C. for 2 hours to obtain about 500 bp fragment. These two fragments were ligated using T4 DNA ligase at 14° C. for 14 hours. Thus, plasmid pIN-tac was obtained.

Figure 6:
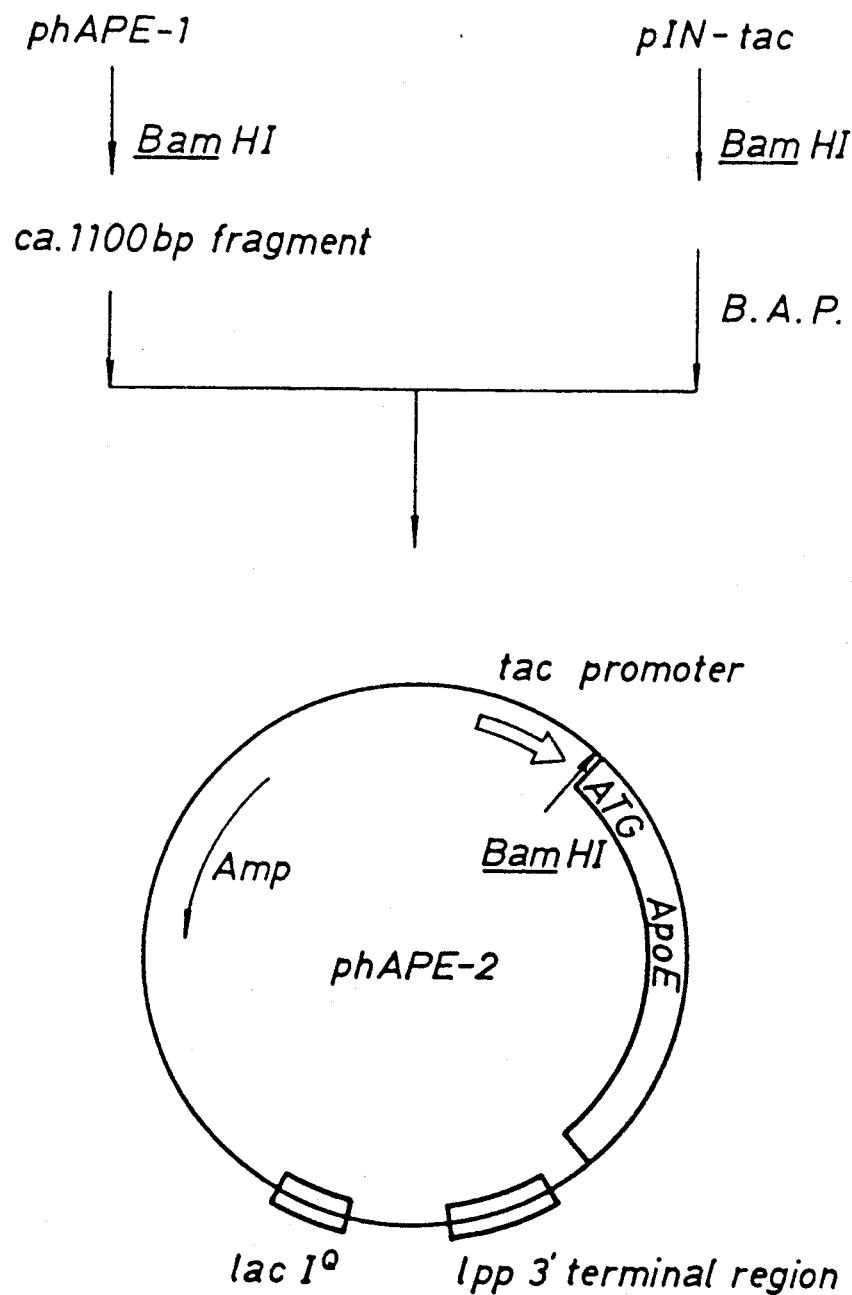

(4) Construction of Plasmid phAPE-2 (FIG. 6)

The plasmid phAPE-1 was digested with BamHI at 37° C. for 2 hours to obtain about 1100 bp fragment. On the other hand, the plasmid pIN-tac was digested with BamHI and treated with B.A.P. The resulting fragment was ligated at 14° C. for 14 hours to the about 1100 bp fragment in the presence of T4 DNA ligase. The resulting plasmid phAPE-2 is shown in FIG. 6, wherein lacI$^Q$ gene is a gene producing a large amount of lacI.

Figure 7:
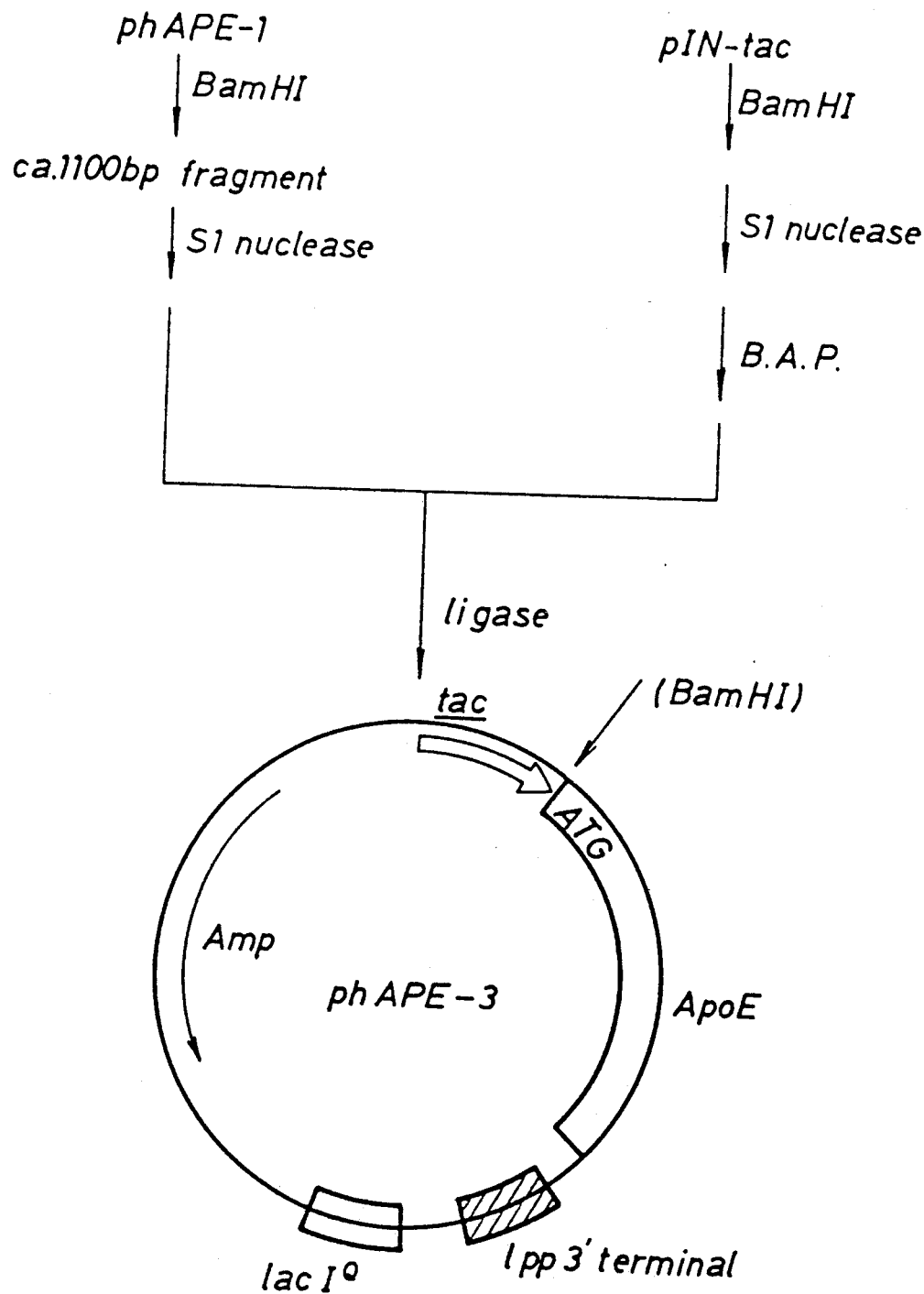

(5) Construction of Plasmid phAPE-3 (FIG. 7)

The plasmid phAPE 1 was digested with BamHI at 37° C. for 2 hours to obtain about 1100 bp fragment. The fragment was treated with S1 nuclease at 37° C. for 30 minutes. On the other hand, the plasmid pIN-tac was digested with BamHI and treated with S1 nuclease and B.A.P. The resulting fragment was ligated to the fragment obtained above from phAPE-1 in the presence of T4 DNA ligase. Thus, plasmid phAPE-3 was obtained.

Figure 8A:
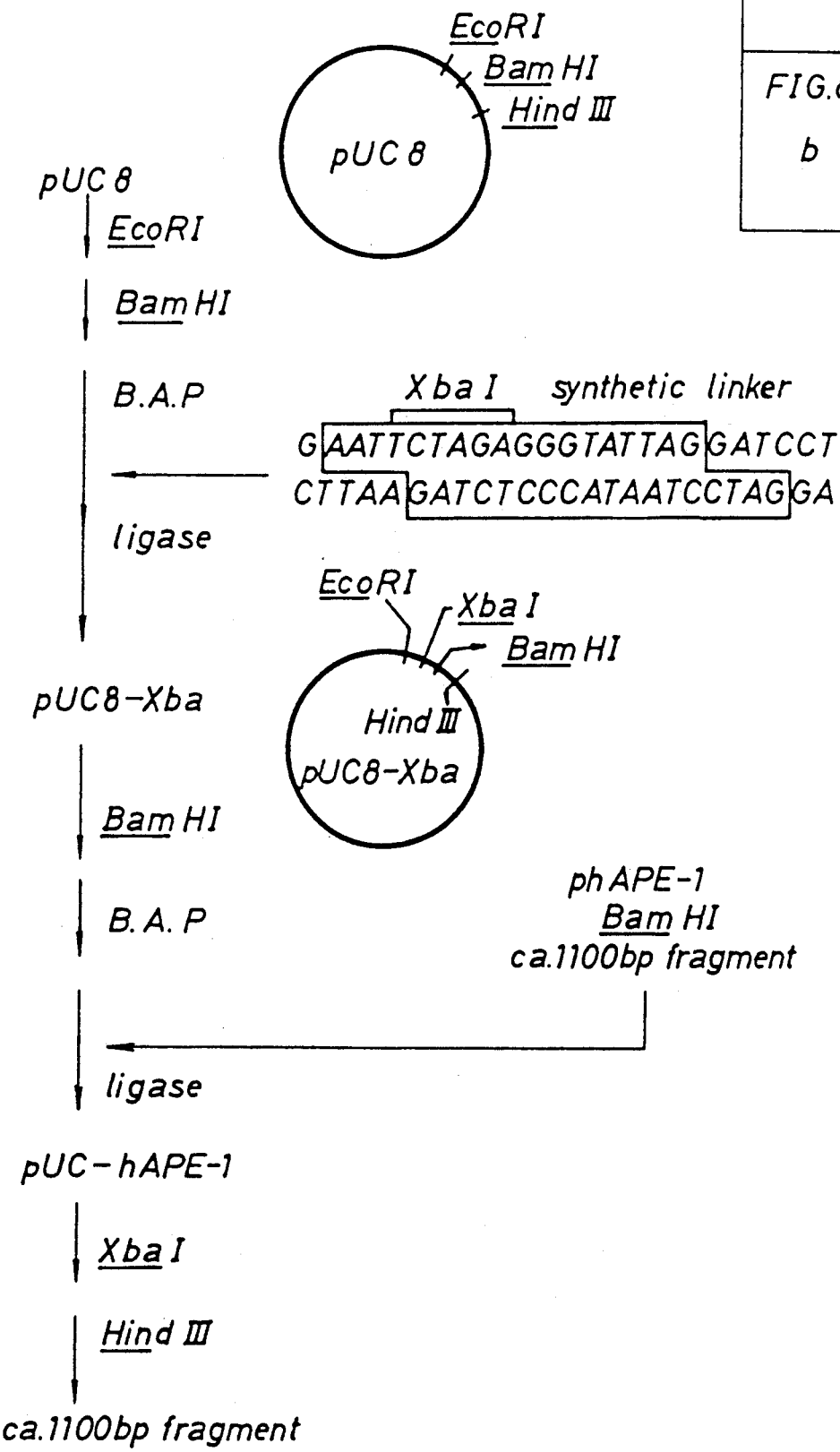
Figure 8B:
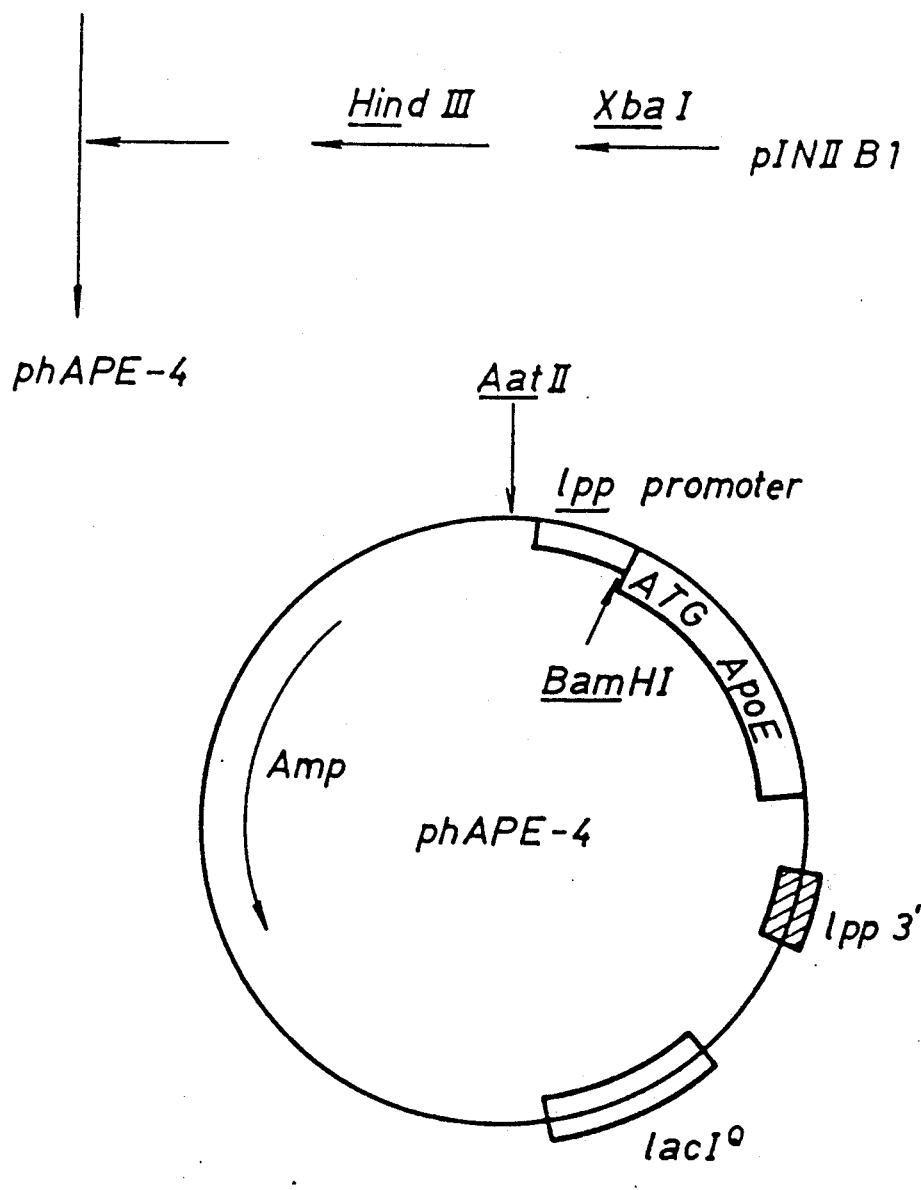

(6) Construction of Plasmid phAPE-4 (FIG. 8)

Plasmid pUC8 [Gene, 19, 259 (1982)] was digested with EcoRI and BamHI at 37° C. for 2 hours and treated with B.A.P. The resulting fragment was ligated to a synthetic linker shown in FIG. 8 in the presence of T4 DNA ligase at 37° C. for 14 hours. Thus plasmid pUC8-Xba was obtained.

The plasmid pUC8-Xba was digested with BamHI at 37° C. for 2 hours and treated with B.A.P. The resulting fragment was ligated using T4 DNA ligase to 1100 bp fragment obtained by digesting phAPE-1 with BamHI. Thus, plasmid pUC-hAPE-1 was obtained.

The plasmid was digested with XbaI and HindIII at 37° C. for 2 hours to obtain about 1100 bp fragment. This fragment was inserted between XbaI and HindIII sites of plasmid pINIIB1 (Experimental Manipulation of Gene Expression, Edited by M. Inouye, 1983, Academic Press, p. 15). Thus, plasmid phAPE-4 was obtained.

B. Production of Proteins

The plasmids phAPE-2, phAPE-3 and phAPE 4 containing DNA fragment of the invention were used to transform *E. coli* HB101. The transformants were cultured in M9-CA medium to produce the proteins. Electrophoresis of the products revealed the production of human apolipoprotein E-like proteins.

EXAMPLE 3

Production of Proteins in Yeast

Figure 9:
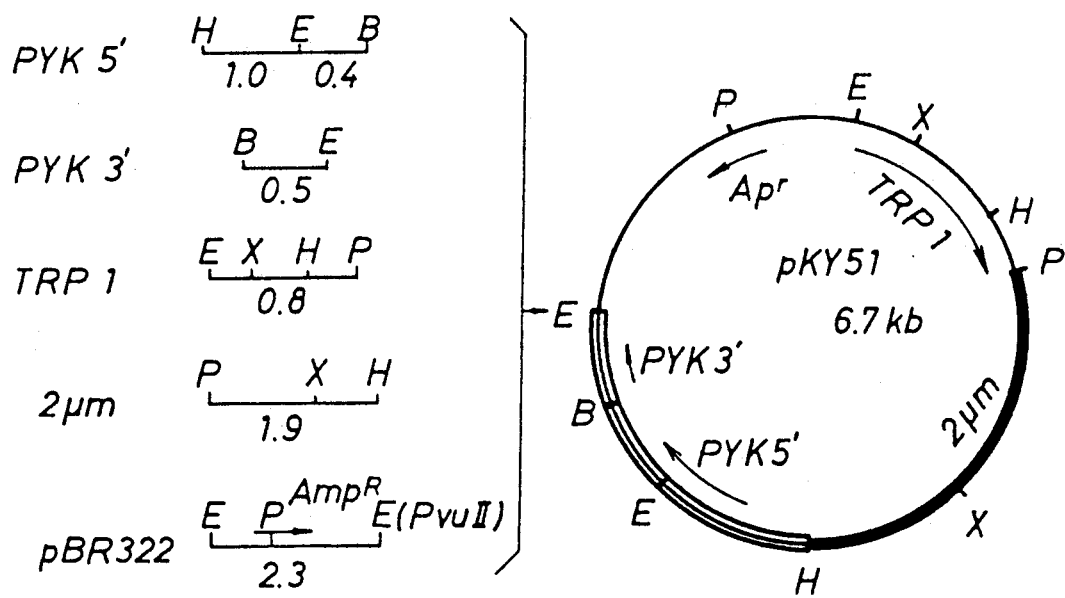
FIG. 9 shows the construction of plasmid pKY51.

A. Construction of Plasmid pKY51 (FIG. 9)

(1) About 8.8 kb HindIII DNA fragment containing pyruvate kinase (PYK) gene was obtained from chromosomal DNA of *Saccharomyces cerevisiae:* The Journal of Biological Chemistry, Vol. 258, No. 4, 2193-2201 (1983).

The HindIII DNA fragment was digested with HaeIII and EcoRL. The HaeIII-EcoRI fragment was ligated to HincII-EcoRI fragment of pUC8. The resulting plasmid was digested with HindIII and EcoRI to obtain 1.0 kb HindIII-EcoRI DNA fragment.

On the other hand, the HindIII DNA fragment was digested with EcoRI and XbaI to obtain EcoRI-XbaI DNA fragment. This fragment was treated with Bal31 exonuclease, filled in using T4 DNA polymerase and ligated to BamHI linker in the presence of T4 DNA ligase. The resulting fragment was cloned into BamHI site of pUC8 and digested with BamHI to obtain BamHI DNA fragment. This DNA fragment was digested with BamHI and AvaII. Thus, AvaII-BamHI DNA fragment was obtained.

The EcoRI-XbaI DNA fragment described above was digested with EcoRI and AvaII. The resulting DNA fragment was ligated to the AvaII-BamHI DNA fragment above in the presence of T4 DNA ligase and then ligated to EcoRI BamHI fragment of pUC8. The resulting plasmid was digested with EcoRI and BamHI to obtain 0.4 kb EcoRI-BamHI DNA fragment.

The 1.0 kb HindIII-EcoRI DNA fragment and the 0.4 kb EcoRI-BamHI DNA fragment were ligated to each other in the presence of T4 DNA ligase. Thus, about 1.4 kb HindIII-BamHI DNA fragment derived from 5'-flanking region was obtained (2) The HindIII DNA fragment containing PYK gene was digested with HaeIII. The resulting 0.5 kb HaeIII DNA fragment was cloned into SmaI site of pUC8 and digested with EcoRI and BamHI. Thus, about 0.5 kb BamHI-EcoRI DNA fragment derived from 3'-flanking region was obtained.

(3) Plasmid YR$_p$7 [Nature, 282, 39-43 (1979)]was digested with EcoRI and PstI to obtain about 0.8 kb EcoRI-PstI DNA fragment containing TRP1 gene.

(4) Yeast 2 μm DNA was digested with PstI and HindIII to obtain about 1.9 kb PstI-HindIII DNA fragment.

(5) Plasmid pBR322 was digested with EcoRI and PvuII. EcoRI linker was added to the PvuII site in the presence of T4 DNA polymerase. Thus, about 2.3 kb EcoRI-EcoRI linker was obtained.

(6) Five DNA fragments obtained in (1)-(5) above were ligated to each other using T4 DNA ligase to obtain pKY51 (about 6.7 kb).

B. Expression of AcoE Protein

The plasmid phAPE-1 was digested with BamHI. The resulting BamHI-BamHI DNA fragment containing ApoE gene was inserted into BamHI site of the plasmid pKY51. The resulting plasmid was used to transform *Saccharomyces cerevisiae* 20B-12. The transformants were cultured in SD medium. Production of ApoE protein was detected by Western Blotting; about 0.5 mg/OD/l.

EXAMPLE 4

Figure 10:
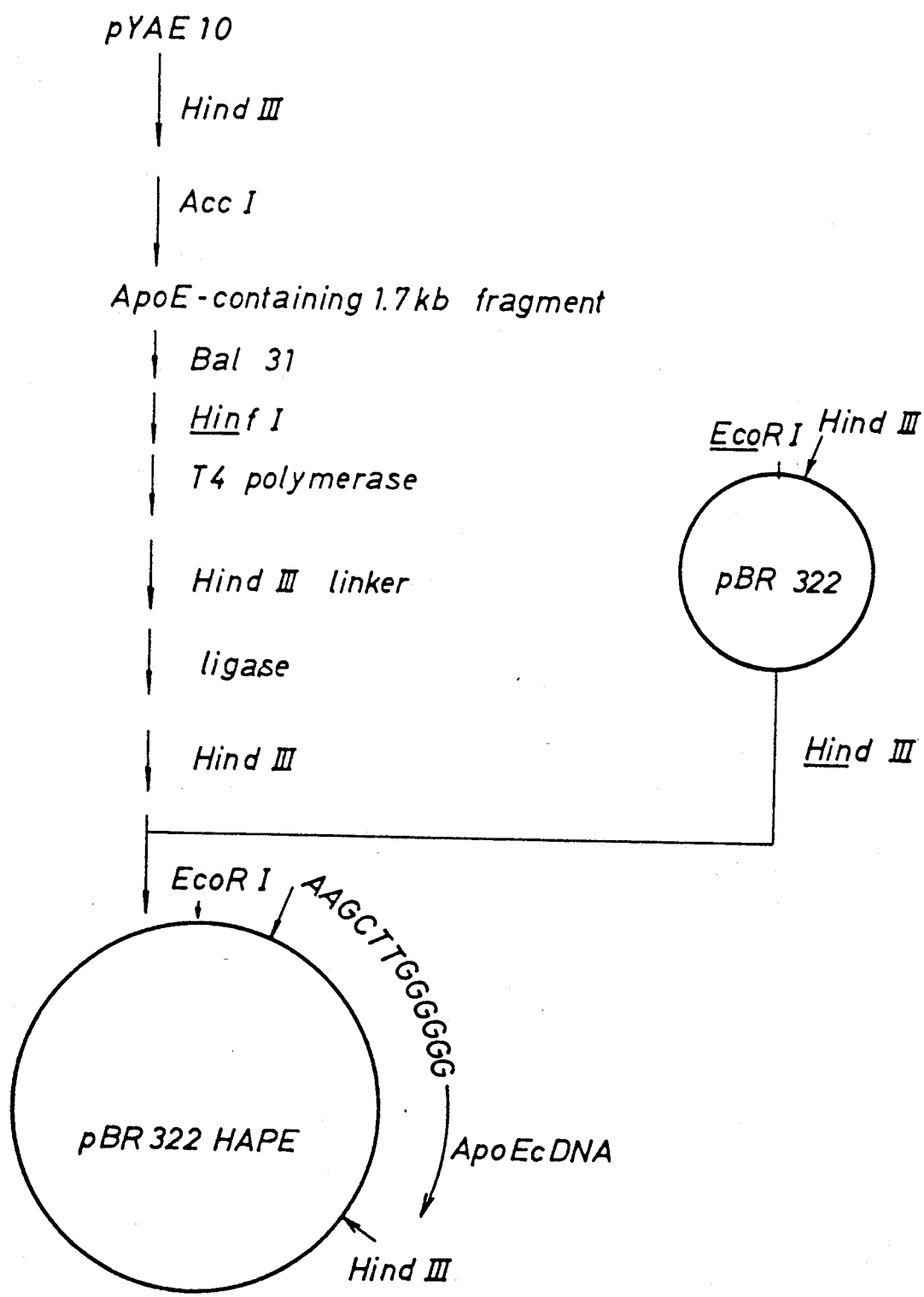
FIG. 10 shows the construction of plasmid pBR322HAPE.

Expression of Human Apolipoprotein E (h-ApoE) in CHO Cells (1) Elimination of Poly(G) and Poly(A) Portions of Apolipoprotein E cDNA (FIG. 10)

The plasmid pYAE10 obtained in Example 1 was digested with HindIII and AccI to obtain 1.7 kb-DNA fragment containing DNA which coded for apolipoprotein E. The DNA fragment was treated with Bal31 exonuclease, digested with HinfI and treated with T4 DNA polymerase to form blunt ends. HindIII linker was ligated to each blunt end in the presence of T4 DNA ligase. The resulting fragment was digested with HindIII and introduced into HindIII site of pBR322. Thus plasmid pBR322HAPE was obtained.

Figure 11:
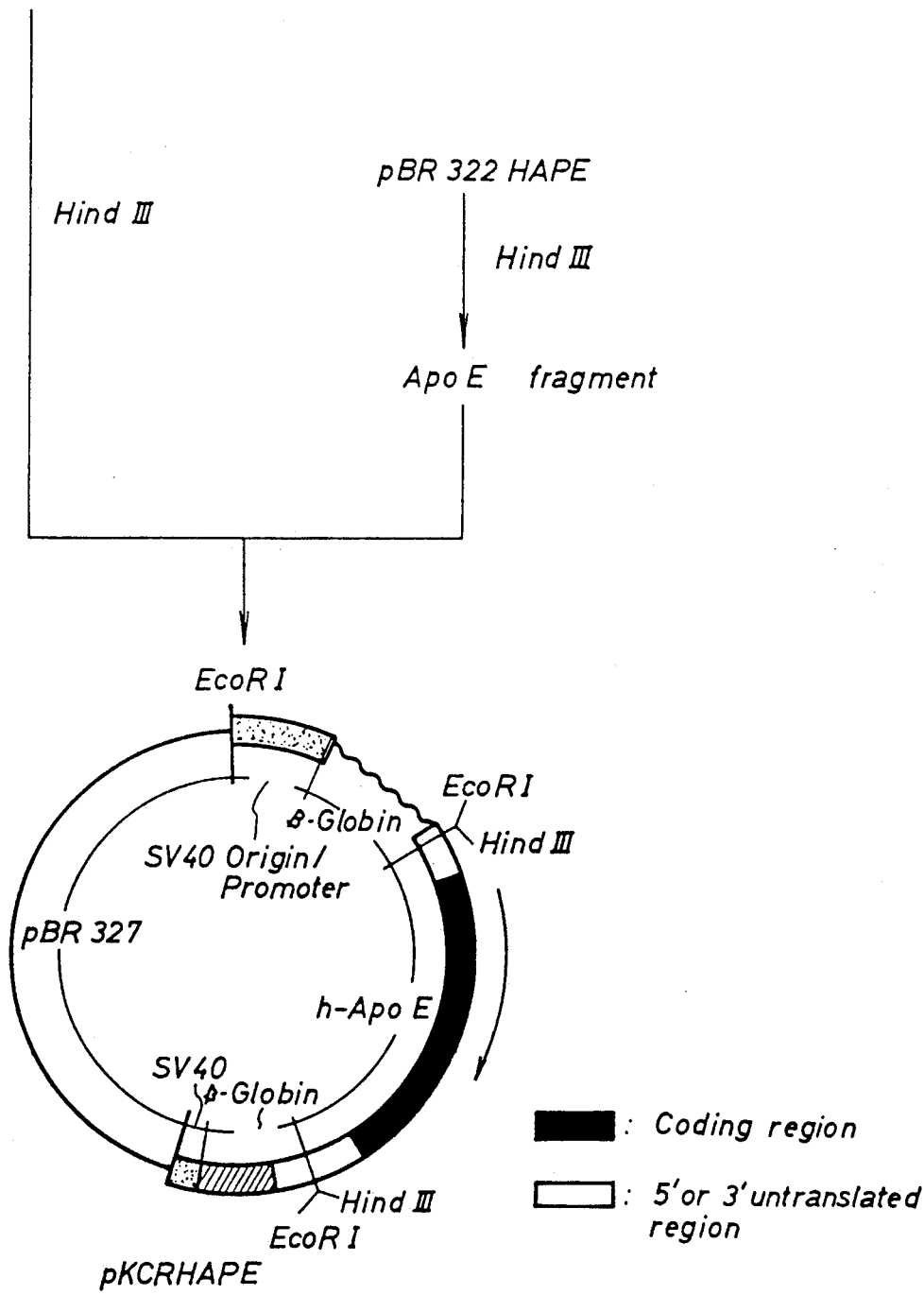
FIG. 11 shows the construction of plasmid pKCRHAPE.

(2) Re-construction of Expression Vector (FIG. 11)

The plasmid pBR322HAPE was digested with HindIII. The resulting HindIII fragment containing DNA which coded for apolipoprotein E was introduced into HindIII site of plasmid pKCRH2 containing SV40 promoter [Nature, 307, 604 (1984)]. Thus plasmid pKCRHAPE was obtained.

(3) Co-transfection of CHO Cells and Production of ApoE

The plasmid pKCRHAPE and plasmid pMTVdhfr containing dhfr gene [Nature, 294, 228 (1981)] were transfected to CHO (dhfr−) cells [Proc. Natl. Acad. Sci., 77, 4216 (1980)] by calcium phosphate method using DNA-calcium phosphate coprecipitate. After two days culture, the cells were subcultured in α-MEM medium (GIBCO No. 410-2000, U.S.A.) which was deficient in thymidine and hypoxanthine. The surviving clone (dhfr+) was isolated. The clones produced ApoE in an amount of about 10 mg/l/day as detected by Western Blot Analysis.

What is claimed is:

1. A method for producing human apolipoprotein E which comprises the steps of (i) providing a culture of CHO cells transformed with a plasmid which contains the human ApoE gene and the SV40 early promoter, wherein expression of human apolipoprotein E by said CHO cells is driven by said promoter, and (ii) isolating from said culture human apolipoprotein E, wherein said CHO cells are obtained from clones that satisfy a yield level for apolipoprotein E of about 10 mg/l/day at a cell density of 10⁶/ml.

2. A method of claim 1, wherein said ApoE gene encodes the amino acid sequence

| Lys | Val | Glu | Gln | Ala | Val | Glu | Thr | Glu | Pro | Glu | Pro | Glu | Leu | Arg |
|-----|-----|-----|-----|-----|-----|-----|-----|-----|-----|-----|-----|-----|-----|-----|
| Gln | Gln | Thr | Glu | Trp | Gln | Ser | Gly | Gln | Arg | Trp | Glu | Leu | Ala | Leu |
| Gly | Arg | Phe | Trp | Asp | Tyr | Leu | Arg | Trp | Val | Gln | Thr | Leu | Ser | Glu |
| Gln | Val | Gln | Glu | Glu | Leu | Leu | Ser | Ser | Gln | Val | Thr | Gln | Glu | Leu |

| | | | | | | | | | | | | |
|---|---|---|---|---|---|---|---|---|---|---|---|---|
| Arg | Ala | Leu | Met | Asp | Glu | Thr | Met | Lys | Glu | Leu | Lys | Ala | Tyr | Lys |
| Ser | Glu | Leu | Glu | Glu | Gln | Leu | Thr | Pro | Val | Ala | Glu | Glu | Thr | Arg |
| Ala | Arg | Leu | Ser | Lys | Glu | Leu | Gln | Ala | Ala | Gln | Ala | Arg | Leu | Gly |
| Ala | Asp | Met | Glu | Asp | Val | CyS | Gly | Arg | Leu | Val | Gln | Tyr | Arg | Gly |
| Glu | Val | gln | Ala | Met | Leu | Gly | Gln | Ser | Thr | Glu | Glu | Leu | Arg | Val |
| Arg | Leu | Ala | Ser | His | Leu | Arg | Lys | Leu | Arg | Lys | Arg | Leu | Leu | Arg |
| Asp | Ala | Asp | Asp | Leu | Gln | Lys | Arg | Leu | Ala | Val | Tyr | Gln | Ala | Gly |
| Ala | Arg | Glu | Gly | Ala | Glu | Arg | Gly | Leu | Ser | Ala | Ile | Arg | Glu | Arg |
| Leu | Gly | Pro | Leu | Val | Glu | Gln | Gly | Arg | Val | Arg | Ala | Ala | Thr | Val |
| Gly | Ser | Leu | Ala | gly | Gln | Pro | Leu | Gln | Glu | Arg | Ala | Gln | Ala | Trp |
| Gly | Glu | Arg | Leu | Arg | Ala | Arg | Met | Glu | Glu | Met | Gly | Ser | Arg | Thr |
| Arg | Asp | Arg | Leu | Asp | Glu | Val | Lys | Glu | Gln | Val | Ala | Glu | Val | Arg |
| Ala | Lys | Leu | Glu | Gly | Gln | Ala | Gln | Gln | Ile | Arg | Leu | Gln | Ala | Glu |
| Ala | Phe | Gln | Ala | Arg | Leu | Lys | Ser | Trp | Phe | Glu | Pro | Leu | Val | Glu |
| Asp | Met | Gln | Arg | Gln | Trp | Ala | Gly | Leu | Val | Glu | Lys | Val | Gln | Ala |
| Ala | Val | Gly | Thr | Ser | Ala | Ala | Pro | Val | Pro | Ser | Asp | Asn | His. | |

3. The method of claim 1, in which the transformed cells contain the plasmid pKCRHAPE.

4. The method of claim 3 wherein the expression of human apolipoprotein E is driven by the SV40 early promoter.

* * * * *